ting the excretion of such materials that have accumulated in the body. The process involves oral administration to a human or lower animal in need of such treatment of a sufficient amount of a non-absorbable polyol fatty acid polyester to effect detoxification.

United States Patent [19]

Volpenhein et al.

[11] 4,241,054

[45] Dec. 23, 1980

[54] DETOXIFYING LIPOPHILIC TOXINS

[75] Inventors: Robert A. Volpenhein; Ronald J. Jandacek, both of Cincinnati, Ohio

[73] Assignee: The Procter & Gamble Company, Cincinnati, Ohio

[21] Appl. No.: 967,658

[22] Filed: Dec. 8, 1978

[51] Int. Cl.³ ............................................. A61K 31/70
[52] U.S. Cl. .................................... 424/180; 536/115; 536/119
[58] Field of Search ................. 424/180; 536/115, 119

[56] References Cited

U.S. PATENT DOCUMENTS

| | | | |
|---|---|---|---|
| 2,893,990 | 7/1959 | Hass et al. | 536/119 |
| 3,251,827 | 5/1966 | Schnell et al. | 536/119 |
| 3,859,318 | 1/1975 | Lesuer | 536/115 |
| 4,005,195 | 1/1977 | Jandacek | 424/180 |
| 4,005,196 | 1/1977 | Jandacek et al. | 424/180 |

*Primary Examiner*—Johnnie R. Brown
*Attorney, Agent, or Firm*—Steven J. Goldstein; Jerry J. Yetter; Michael J. Roth

[57] ABSTRACT

Non-absorbable polyol polyesters dissolve toxic lipophilic compounds in the stomach and intestine of humans and lower animals and thus decrease their absorption. The polyol polyesters also dissolve the toxic, lipophilic materials and their metabolites if they are excreted in bile, and prevent their resorption. The invention thus provides a means for detoxifying humans and lower animals which have ingested toxic lipophilic materials (e.g., DDT, Kepone, PCB, PBB) by accelerating the excretion of such materials that have accumulated in the body. The process involves oral administration to a human or lower animal in need of such treatment of a sufficient amount of a non-absorbable polyol fatty acid polyester to effect detoxification.

15 Claims, No Drawings

DETOXIFYING LIPOPHILIC TOXINS

TECHNICAL FIELD

A variety of lipophilic toxins commonly used in industrial and agricultural applications have at one time or another found their way into the food chain of humans and lower animals. These toxins include insecticides, such as DDT and Kepone; herbicides, such as PCP; and a variety of halogenated and nonhalogenated industrial chemicals, examples of which include the polychlorinated biphenyls, or PCB's, which are used as cooling and insulating liquids in electrical equipment, and polybrominated bisphenols, or PBB's, which are used as fire retardant additives in plastics.

Current methods of treating exposure to lipophilic toxins involve combination therapy which employs symptomatic treatment and systemic support with simple attempts to improve elimination of the toxins via emetics and enemas, and, according to some authorities, administration of mineral oil to reduce absorption of the toxins. Such methods are not entirely successful and, because of the obvious discomfort associated with the use of emetics, laxatives, and enemas, their use is limited to those acute situations in which a specific incident of accidental ingestion of a lipophilic toxin has been identified. Moreover, mineral oil is partially absorbed by the body and undesirably deposits in the liver. Thus, even the problem of recognized, acute exposures to such toxins lacks an entirely satisfactory solution.

The more insidious problem of low-level contamination of foodstuffs by trace amounts of lipophilic toxins such as DDT and PCP often goes unrecognized for long periods. Yet, because such toxins are lipophilic, they accumulate in the fat depots of the body as a result of long term exposure. The long-term subclinical toxic effects resulting from low level contamination with such toxins remain a topic of active investigation.

Contamination by lipophilic toxins at lower points in the human food chain, such as contamination of grain and other vegetable products, contamination of animal feeds, and contamination of animals themselves, with the resulting contamination of animal by-products such as meat, eggs and dairy products, has been a problem heretofore solved only by the destruction of the affected materials or animals.

Non-absorbable polyol fatty acid polyesters of the type disclosed herein provide a safe, effective means for both acute and chronic detoxification of humans and lower animals which have been exposed to lipophilic toxins.

BACKGROUND ART

A variety of therapeutic regimens have been used for treating acute exposure to lipophilic toxins, and these primarily employ systemic support in combination with measures to reduce absorption and improve elimination, such as emetics and enemas. None of these are entirely satisfactory for treating an acute poisoning, and by their nature all of them are unsuitable for detoxification following chronic exposure.

White mineral oils or "paraffin oils" are polycyclic high-boiling petroleum fractions that have been decolorized by activated diatomaceous clay or crude aluminum oxide. C. R. Noller, *Chemistry of Organic Compounds*, 2nd. Ed. (1957). p. 82. Mineral oil is a well-known laxative and has been suggested for use as a kind of "intestinal solvent" to dissolve lipophilic toxins and cause their removal in bodily wastes. S. Moeschlin, *Klinik and Therapie der Vergiftungen*, 4th Ed. (1964); Richter, E., *Chemosphere* 6(6):357-369 (1977). However, mineral oil is partially absorbed by the body and undesirably deposits in the liver and other tissues. E. Fingl, "Laxatives and Cathartics" in *The Pharmacological Basis of Therapeutics*, 5th Ed., (1975), L. S. Goodman and A. Gilman, eds., p. 978. See also Becker, G. L., *Am. J. Dig. Dis.* 1952, 19:355-348. The polyesters herein, in contrast with mineral oil, are not absorbed and/or deposited in the liver during usage in a treatment/prevention regimen. Coh, W. J., et al., *N. Eng. J. Med.* 298(5):243-248 (1978) discloses the use of cholestryamine, an ion-exchange resin, to treat the toxic effects of Kepone.

Treatment of endogenous disease states, such as hypercholesterolemia, with the polyesters employed in the present invention is known to the art. Relevant patents include: U.S. Pat. No. 3,600,186 issued Aug. 17, 1971 to Mattson, et al,, which discloses and claims a low calorie, fat-containing food composition where from about 10% to about 100% of the total fat consists of polyol fatty cid polyesters.

U.S. Pat. No. 3,954,976 issued May 4, 1976 to Mattson, et al., encompasses polyol fatty acid polyesters in 0.1-5 gram unit doses as pharmaceutical compositions for inhibiting the absorption of cholesterol.

U.S. Pat. No. 3,963,699 issued June 15, 1976 to Rizzi, et al., relates to a solvent-free esterification process for preparing the polyol fatty acid polyesters. A sugar, a fatty acid $C_1-C_2$ alkyl ester, an alkali metal fatty acid soap and a base catalyst (alkali metal alloys, alkali metal hydrides, alkali metal alkoxides) are heated to form a homogeneous melt; excess fatty acid alkyl ester is added to form the polyol fatty acid polyester, which is then separated from the mixture. The process allows drug-quality polyol fatty acid polyesters to be manufactured without a solvent-removal step.

U.S. Pat. No. 4,005,195 issued Jan. 25, 1977 to Jandacek describes anti-anal leakage (AAL) agents used in combination with the liquid polyol fatty acid polyesters. The disclosure relates to: (1) compositions of matter comprising polyol fatty acid polyesters + anti-anal leakage compounds; (2) low calorie foods with polyol fatty acid polyesters + AAL compounds; (3) polyol fatty acid polyesters + AAL in unit dose form (0.1-5 grams) as pharmaceuticals; and (4) methods for treating hypercholesterolemia by inhibiting absorption of cholesterol without anal leakage by administering compositions per (1).

U.S. Pat. No. 4,005,196 issued Jan. 25, 1977 to Jandacek, et al., encompasses compositions comprising fat-soluble vitamins in combination with polyol fatty acid polyesters and anti-anal leakage agents.

U.S. Pat. No. 4,034,083 issued July 5, 1977 to Mattson, discloses polyol fatty acid polyesters + fat-soluble vitamins.

The disclosures of the foregoing patents are incorporated herein by reference.

DISCLOSURE OF INVENTION

The present invention is based on the discovery that certain liquid polyesters, while not digested or absorbed in the body of humans or lower animals, essentially dissolve and remove fat-soluble toxins from the body. The invention thus provides a means for treating both acute and chronic exposures to lipophilic toxins.

The present invention employs certain non-absorbable, non-digestible polyol fatty acid polyesters, which are described more fully hereinafter. The polyol fatty acid polyesters used herein can be effectively used either "neat", or, because their physical and chemical properties are similar to commonly used digestible fats and oils, e.g., salad and cooking oils, they can be incorporated into foods in addition to or in lieu of the digestible, absorbable fats and oils now used, or incorporated into animal feed mixes, so that detoxification of humans and lower animals which are chronically exposed to lipophilic organic toxins can be continuously effected via a dietary regimen.

Polyol fatty acid polyesters also provide a means for continuously decontaminating the human food chain, both by incorporation into animal feeds and by direct administration to animals which serve as food sources, thereby reducing the absorption of lipophilic toxins by the animal and enhancing elimination of such toxins acquired through previous exposures. In the same way, polyol fatty acid polyesters can be used to treat lipophilic toxin poisoning of household pets, or the like.

POLYOL POLYESTERS

The polyol polyesters (or, simply, "polyesters") employed in this invention comprise well-defined polyol fatty acid esters. The polyol starting material must have at least four esterifiable hydroxyl groups. Examples of suitable polyols are sugars, especially monosaccharides and disaccharides, and sugar alcohols. Examples of monosaccharides containing four hydroxyl groups are xylose and arabinose and the sugar alcohol derived from xylose, i.e., xylitol. The monosaccharide erythrose starting material is not suitable for the practice of this invention since it only contains three hydroxyl groups but the sugar alcohol derived from erythrose, i.e., erythritol, contains four hydroxyl groups and accordingly can be used. Suitable five hydroxyl group-containing monosaccharides are galactose, fructose, and sorbose. Sugar alcohols containing six hydroxyl groups derived from sucrose, glucose, and sorbose, e.g., sorbitol, are also suitable. Examples of disaccharide polyols which can be used include maltose, lactose, and sucrose, all of which contain eight hydroxyl groups.

Preferred polyols for preparing the esters for use in the present invention are selected from the group consisting of erythritol, xylitol, sorbitol, glucose and sucrose. Sucrose is especially preferred.

The polyol starting material having at least four hydroxyl groups must be esterified with a fatty cid having from about eight to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers, depending on the desired physical properties, for example liquid or solid, of the polyol fatty acid ester compound.

Fatty acids per se or naturally occurring fats and oils can serve as the source of the fatty acid component in the polyol fatty acid ester. For example, rapeseed oil provides a good source for $C_{22}$ fatty acid. $C_{16}$-$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component. Among the fatty acids, those that are preferred have from about 14 to about 18 carbon atoms, and are most preferably selected from the group consisting of myristic, palmitic, stearic, oleic, and linoleic fatty acids. Thus, natural fats and oils which have a high content of these fatty acids represent preferred sources for the fatty acid component of the polyol polyesters used herein.

The polyol fatty acid esters useful in this invention must contain at least four fatty acid ester groups. Polyol fatty acid ester compounds that contain three or less fatty acid ester groups tend to be digested in the intestinal tract in much the same manner as ordinary triglyceride fats, whereas the polyol fatty acid ester compounds that contain four or more fatty acid ester groups are substantially non-absorbable and non-digestable by the human body. It is not necessary that all of the hydroxyl groups of the polyol be esterified with fatty acid, but it is preferable that the polyol polyester contain no more than two unesterified hydroxyl groups. Most preferably, all of the hydroxyl groups of the polyol are esterified with fatty acid, i.e., the compound is substantially completely esterified. The fatty acid ester groups can be the same or mixed on the same polyol polyester molecule.

Thus, to illustrate the above points, the sucrose triester of fatty acid would not be suitable for use herein because it does not contain the required four fatty acid ester groups. Sucrose tetra fatty acid ester would be suitable but is not preferred because it has more than two unesterified hydroxyl groups. Sucrose hexa fatty acid ester would be preferred because it has no more than two unesterified hydroxyl groups. An example of a highly preferred compound in which all of the hydroxyl groups are esterified with fatty acid is sucrose octa fatty acid ester.

The following are examples of suitable polyol fatty acid esters containing at least four fatty acid ester groups suitable for use in the present invention: glucose tetraoleate; glucose tetrastearate; glucose tetraester of mixed soybean oil fatty acids; mannose tetraester of tallow fatty acids; galactose tetraester of olive oil fatty acid; arabinose tetraester of cottonseed oil fatty acid; xylose tetralinoleate; galactose pentastearate; sucrose hexaoleate; sucrose octaoleate; sucrose octaester of substantially completely hydrogenated soybean oil fatty acid; sucrose octaester or peanut oil fatty acid. As noted before, highly preferred polyol fatty acid esters are those wherein the fatty acids contain from about 14 to about 18 carbon atoms and are thus derived from such natural materials as soybean oil, tallow, palm oil and olive oil. Examples of such compounds are the erythritol tetraester of olive oil fatty acid, erythritol tetraoleate, xylitol pentaoleate, sorbitol hexaoleate, sucrose octaoleate, and sucrose octaester of soybean oil fatty acid.

The polyol fatty acid esters suitable for use in this invention can be prepared by a variety of methods well known to those skilled in the art. These methods include: transesterification of the polyol with methyl, ethyl or glycerol fatty acid esters, acylation with a fatty acid chloride; acylation with a fatty acid anhydride and acylation with a fatty acid per se. As an example, the preparation of polyol fatty acid esters is described in U.S. Pat. Nos. 2,831,854 and 3,521,827.

A method of preparing polyol fatty acid polyesters which is especially preferred for the food and pharmaceutical compositions employed herein because it is solvent-free, does not generate difficult-to-remove contaminants, and produces high yields, is described in U.S. Pat. No. 3,963,699, incorporated herein by reference.

It is to be understood that the polyol polyesters disclosed herein can be used separately, and do not require conjoint use with anti-anal leakage agents and vitamins to effect detoxification of humans and lower animals. However, the use of anti-anal leakage agents and/or vitamins conjointly with the polyesters avoids undesirable side effects in patients undergoing a prolonged treatment regimen.

ANTI-ANAL-LEAKAGE AGENTS

In past studies of liquid polyesters, rats which ingested about 300 mg. to about 3000 mg. total liquid polyester per day and human volunteers who ingested from about 10 grams to about 50 grams total liquid polyester per day exhibited undesired anal leakage of the polyesters, a direct result of passage of the polyesters through the anal sphincter. By combining the liquid polyester compositions with an anti-anal leakage agent, this undesired anal leakage effect is prevented. The detoxifying effect of the liquid polyesters is not diminished. (By "anti-anal leakage agent", or "AAL" agent, herein is meant those materials which prevent frank leakage of the liquid polyesters. The natural stool-softening effect of the polyesters is not substantially affected, nor is it a problem.)

It is to be understood that the edible, non-absorbable, non-digestible polyester materials which cause anal leakage are liquids at body temperature, i.e., have a melting point of ca. 37° C., or below. Edible, non-absorbable, non-digestible polyester materials that are solid at body temperature do not exhibit the undesirable anal leakage effects noted with the liquid polyesters. Indeed, such solid polyesters can be used as one type of AAL agent herein. In general, the liquid polyesters are thiose which are made from unsaturated fatty acids, whereas the solid polyesters are substantially saturated.

One class of materials which provide the anti-anal leakage effect herein includes fatty acids having a melting point of ca. 37° C. or higher, and ingestible, digestible sources of such fatty acids. The fatty acid AAL agents include, for example, the $C_{12}$–$C_{24}$ saturated fatty acids, and ingestible, digestible sources thereof.

Highly preferred herein for their anti-anal leakage effect are the $C_{16}$–$C_{22}$, most preferably $C_{16}$–$C_{18}$, saturated fatty acids, or edible sources thereof.

Specific examples of materials useful as the foregoing type of AAL agent herein include natural or processed fats yielding $C_{12}$–$C_{24}$ saturated fatty acids in the gut, e.g., materials such as cocoa butter, palm oil, palm kernel oil, coconut oil, tallow, lard, enriched concentrates of triglycerides having high levels of saturated fatty acids obtainable from these sources and sources such as highly saturated cottonseed oil fractions obtained by processes such as crystallization or directed rearrangement which yield the desired higher concentrations of the more saturated fatty acids in the resulting "hardstock" fractions. Such materials are all available by well known processes.

Partialy hydrogenated oils, including all of the above, as well as partially hydrogenated soybean oil, safflower seed oil, rapeseed oil, or such materials which are hydrogenated and concentrated, for example by crystallization, to provide fractions which are enriched in sources of the longer-chain, substantially saturated fatty acids, are all useful as the AAL agent herein. (By "substantially hydrogenated" herein is meant oils having an iodine value of ca. 30, or lower.)

Of course, any of the foregoing unsaturated oils are useful herein after they have been substantially completely hydrogenated to convert the unsaturated fatty acid (ester) groups to the corresponding saturated fatty acids.

Synthetic AAL materials, especially fatty acid esters made from the $C_{12}$–$C_{24}$, more preferably $C_{16}$–$C_{22}$, most preferably $C_{16}$–$C_{18}$, saturated fatty acids are useful herein. Such materials include the esters of tetrahydric alcohols such as erythritol, esters of pentahydric alcohols such as xylitol, and esters of hexahydric alcohols such as sorbitol, and the like.

The $C_{12}$–$C_{24}$ saturated fatty acid esters of monohydric alcohols such as methyl, ethyl, and propyl alcohols (preferably ethyl alcohol) are also useful AAL's herein. Esters of dihydric alcohols such as 1,2-propanediol, 1,3-butanediol, and the like, can also be used.

Highly preferred AAL agents herein which yield the foregoing fatty acids on hydrolysis in the gut are those which, in combination with the liquid polyesters herein, provide compositions having aesthetically pleasing organoleptic qualities, i.e., better "mouth feel". Such aesthetically pleasing materials include naturally occurring cocoa butter and various synthetic cocoa and confectioners' butters. These preferred AAL agents include, for example, the so-called "position-specific" triglycerides such as 1-stearoyl diolein (SOO); 2-oleoyl-1,3-distearin (SOS); or the corresponding compounds wherein the stearoyl group is replaced by palmitoyl, arachidoyl or behenoyl groups (POO, AOO, BOO; and POP, AOA, BOB, respectively). Another class of aesthetically preferred anti-leakage agents herein are 1-oleoyl distearin (OSS), 1-palmitoyl distearin (PSS), 1-arachidoyl distearin (ASS) and 1-behenoyl distearin (BSS).

These highly preferred, position-specific triglycerides which can be used as a fatty acid source-type of AAL agent herein can be prepared according to the methods described in U.S. Pat. No. 3,809,711, issued May 7, 1974, the disclosures of which are incorporated herein by reference.

The foregoing types of AAL agents appear to function by providing a saturated fatty acid in the gut, said fatty acid thereafter presumably forming an insoluble calcium or magnesium soap in situ. This soap then appears to provide the "stiffening" effect on the liquid polyester, thereby preventing the undesirable anal leakage effect. As noted hereinabove, the solid polyester materials of the present type (i.e., solid, edible, but non-digestible, non-absorbable polyesters) do not cause the undesirable anal leakage effect. It has been determined that these solid polyester materials can also be used as an AAL agent and these represent a second class of AAL agents herein. Since these solid polyester materials do not hydrolyze in the gut to form free fatty acids, or calcium or magnesium fatty acid soaps, their anti-anal leakage effect must be the result of a different mechanism from that which operates with the hydrolyzable esters and fatty acid sources described immediately hereinabove. Presumably, the combination of the solid polyester with the liquid polyesters simply provides a stiffening effect due to some type of crystallization or phase change within the gut.

Typical examples of edible, solid, non-absorbable, non-digestible polyester AAL agents herein include sucrose octastearate, sucrose octapalmitate, sucrose heptastearate, xylitol pentastearate, galactose pentapalmitate, and like, saturated polyol polyesters having at least four—OH groups esterified with $C_{10}$–$C_{22}$ saturated fatty acids.

Another type of edible AAL agent herein comprises fatty acids esters which are non-digestible by virtue of branching on the α-carbon atom of the fatty acid moiety. Such materials, which are well known in the chemical arts, include, for example, α-methyl and α,α-dimethyl $C_{10}$–$C_{18}$ fatty acid esters of lower alcohols such as ethanol and of polyols such as glycerol.

VITAMINS

The physicochemical properties which make the polyol fatty acid polyesters so useful in preventing uptake of toxins by the body are the self-same properties which undesirably interfere with uptake of fat-soluble vitamins. This type of interference with the absorption of vitamins A and E has been demonstrated in human volunteers who consumed polyol fatty acid polyesters. The consequence of polyol fatty acid polyester ingestion was a drop in the blood (plasma) levels of these vitamins.

To prevent the vitamin depletion problem, the polyol polyesters used herein can be fortified with fat-soluble vitamins, especially vitamin A, vitamin E and vitamin D, and mixtures thereof. (The polyesters can also be fortified with vitamin K. However, since the body can synthesize vitamin K, supplementation of the polyesters therewith is probably not critical to adequate nutrition in the normal subject.)

BEST MODE

As can be seen from the foregoing, the present invention provides a method for detoxifying humans and lower animals exposed to lipophilic toxins, comprising orally administering to a human or lower animal exposed to lipophilic toxins a therapeutically effective amount of a non-absorbable, non-digestible polyol fatty acid polyester having at least 4 fatty acid ester groups. Preferred polyol fatty acid polyesters used herein are selected from the group consisting of sugars and sugar alcohols containing from 4 to 8 hydroxyl groups esterified with fatty acid groups, wherein each fatty acid group has from about 8 to about 22 carbon atoms. Most preferred are the sucrose, hexa-, hepta-, and octaesters of oleic acid and mixtures thereof.

In general, the preferred liquid polyol fatty acid polyesters are administered at a rate from about 0.3 mg. liquid polyester per kilogram of body weight per day to about 3 gms. liquid polyester per kilogram of body weight per day.

As disclosed, prolonged oral administration of the liquid polyol fatty acid polyesters in the manner of this invention can lead to leakage of the polyester through the anal sphincter. Anti-anal leakage agents effectively overcome this problem. Highly saturated vegetable oils such as hydrogenated palm oil are most effective on a per-gram basis as AAL agents, while natural and synthetic cocoa and confectioners' butters, including the position specific triglycerides, are organoleptically preferred. Thus, the invention also encompasses a method for detoxifying humans and lower animals exposed to lipophilic toxins with minimal anal leakage effect, comprising orally administering to a human or lower animal exposed to lipophilic toxins a therapeutically effective amount of a composition comprising from about 50% to about 90% by weight of a non-absorbable, non-digestible liquid polyol fatty acid polyester having at least 4 fatty acid ester groups, and from about 10% to about 50% by weight of an anti-anal leakage agent.

A relatively minor problem associated with prolonged administration of both the preferred liquid and the solid polyol fatty acid polyesters in the manner of this invention involves the depletion of the body's stores of certain fat-soluble vitamins. This can be overcome by administering fat-soluble vitamins with the polyester during the detoxification treatment. Thus, the invention also encompasses a method for detoxifying humans and lower animals exposed to lipophilic toxins without decreasing the body's stores of fat-soluble vitamins comprising orally administering to a human or lower animal exposed to lipophilic toxins a therapeutically effective amount of a composition comprising a major portion of a non-absorbable, non-digestible polyol fatty acid polyester (especially the liquid polyesters) having at least 4 fatty acid ester groups, and sufficient fat-soluble vitamin selected from the group consisting of vitamin A, vitamin D, vitamin E, and vitamin K, and mixtures thereof, to prevent abnormally low levels of said fat-soluble vitamins in humans or animals ingesting said composition.

When a patient is on a long-term detoxification regimen, both the anal leakage problem and the vitamin depletion problem are prevented by using highly preferred compositions of the following type:

a. from about 50% to about 90% of a non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms;

b. from about 10% to about 50% by weight of an anti-anal leakage agent selected from the group consisting of: edible $C_{12}$–$C_{24}$ saturated fatty acids, and their edible salts; edible, digestible sources of $C_{12}$–$C_{24}$ saturated fatty acids, solid, edible, non-absorbable, non-digestible polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids; and c. sufficient fat-soluble vitamin selected from the group consisting of vitamin A, vitamin D, vitamin E and vitamin K, and mixtures thereof, to prevent abnormally low levels of said fat-soluble vitamins in animals ingesting said composition.

METHODS OF ADMINISTRATION

The dosages described herein can be administered orally, including any suitable unit dosage form such as pills, tablets, and capsules. A preferred unit dosage form is capsules made from gelatin. The dosages can also be administered "neat," for example, by nasogastric tube in the comatose patient, or as part of a controlled dietary regimen, e.g., as a synthetic salad oil or cooking oil or fat.

The pharmaceutical compositions employed herein can comprise the polyester agent alone, in combination with vitamins, anti-anal leakage agents, or both, either directly or in combination with any desired, non-interfering pharmaceutical carrier. As used herein, the term "pharmaceutical carrier" means a solid or liquid filler, diluent or encapsulating substance. Some examples of the substances which can serve as pharmaceutical carriers are sugars such as lactose, glucose and sucrose; starches such as corn starch and potato starch; cellulose and its derivatives such as sodium carboxymethylcellulose, ethylcellulose, and cellulose acetate; powdered tragacanth; malt; gelatin; talc; oils such as peanut oil, cottonseed oil, sesame oil, olive oil, corn oil and soybean oil; polyols such as propylene glycol, glycerin, sorbitol, mannitol, and polyethylene glycol; agar; alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives can also be present in the compositions, according to the desires of the formulator.

The pharmaceutical carriers of the foregoing type can optionally be employed in conjunction with the polyesters herein to provide practical size-to-dosage relationship composition forms which can be easily ingested, and means for providing accurate unit dosages in a convenient form. The pharmaceutical carrier usually will comprise from about 5% to about 50% by weight of the total pharmaceutical composition.

Since they are not unlike cooking and salad oils and fats in their physical properties, the liquid polyesters employed in the present invention can be used as a partial or total replacement for normal triglyceride fats in any fat-containing food composition, to effect long-term detoxification. In order to achieve these benefits in a reasonable time, it is necessary that at least about 10% of the fat in the food composition comprises the polyesters herein. Highly desirable food compositions are those wherein the fatty component comprises up to about 100% of the polyester/anti-anal leakage compositions herein. Accordingly, the disclosed polyol polyester compositions can be used as a partial or complete replacement for normal triglyceride fats in a salad or cooking oil, or in plastic shortenings for use in frying, cake making, bread making, and the like. The compositions can also be used as partial or complete replacements for normal triglyceride fats in fat-containing food products such as mayonnaise, margarine, and dairy products.

TYPICAL FORMULATIONS

The total AAL agent employed in any of the compositions herein will depend somewhat on the total amount of of liquid polyester being ingested per day. The anti-anal leakage agent should be present in an amount equaling at least about 10% by weight of the liquid polyester. It is more preferred that the AAL agent comprises at least about 20% by weight of the liquid polyester to ensure that anal leakage does not occur, even at high ingestion rates. Compositions wherein the weight of AAL agent comprises from about 20% to about 50% of the weight of liquid polyester provide excellent detoxification without anal leakage of the liquid polyol polyester.

Compositions comprising edible fatty acids, their edible salts or their edible, digestible esters as the AAL agent preferably comprise from about 10% to about 50% of these materials by weight of polyester. Compositions using the palatable position-specific triglycerides as the AAL agent preferably comprise about 20% to about 40% (by weight of liquid polyester) of these AAL agents. When the edible, non-digestible solid polyesters are used as the AAL agent, they are preferably used at a rate of from about 20% to about 50% by weight of the liquid polyester.

The amount of the individual fat-soluble vitamins used to fortify the present compositions will vary with the age of the recipient, the dosage regimen used, and the amount of the vitamin ingested from other dietary sources. For example, in younger, growing children or in pregnant females it is recognized that larger amounts of any given vitamin should be ingested to supply optimal nutritional benefits than are needed with adult males. If the user of the present compositions happens to ingest foods which are extremely rich in a given fat-soluble vitamin, less of that vitamin need be used in the present compositions to insure adequate intestinal uptake for good nutrition. In any event, an attending physician can, if so desired, measure the amount of the fat-soluble vitamins A and E in the plasma. Based on these data, the appropriate type and amount of fat-soluble vitamin used to fortify the polyesters herein can then be determined on an individual basis.

More simply, the formulator of the compositions herein can fortify the polyesters with a recommended daily allowance (RDA), or increment or multiple of an RDA, of any of the fat-soluble vitamins to insure that the user of the compositions will maintain a nutritionally adequate uptake of said vitamins. For example, with vitamin A a daily amount in the range of 20 international units (I.U.) to about 57 I.U. per kilogram of body weight can be employed. With vitamin D, fortification of the compositions to provide about 400 I.U., total, per day is ample. When supplementing with vitamin E, the amount of the vitamin optimal for dietary intake ranges from 3–6 I.U. for infants to 25–30 I.U., total, per day, for adults. When supplementing with vitamin K, it is more difficult to estimate the amount to be ingested to provide adequate nutrition since the microorganisms living in the intestine can synthesize this vitamin. However, it is known that ingestion of from 0.5 mg. −1 mg. of vitamin K per day will prevent insufficiency.

As can be seen from the foregoing, the amount of the fat-soluble vitamins employed herein to fortify the polyesters can vary. In general in the preferred practice of the present invention, the polyesters are fortified with sufficient fat-soluble vitamin to provide from about 0.08% to about 150% of the average RDA.

DOSAGE

It is to be understood that selection of the dosage level and schedule for an appropriate risk/benefit ratio should be made by an individual familiar with the medical management of acute and chronic poisonings, with consideration given to the age, sex, size, fat mass/lean body mass ratio, and duration, route and severity of exposure to lipophilic toxin of the particular individual being treated. Dosage level and dosage timing will also depend on levels of toxin and toxin metabolites found in blood, tissues, vomitus, and feces; toxicity of the particular toxin ingested; expected rates of toxin absorption, biotransformation, and excretion; whether the exposure is acute (presumably high-level) or chronic (presumably low-level), and whether exposure has ceased (therapy) or is expected to continue (prophylaxis).

In both therapeutic and prophylactic regimens the dosage of the compositions herein can vary with the severity of the toxic exposure and the duration of the treatment. Individual dosages for both humans and lower animals can range from about 0.01 mg./kg. to about 500 mg./kg., and greater (unless otherwise specified, the unit designated "mg./kg." as used herein refers to mg. of polyol polyester per kilogram of body weight), preferably from about 0.1 mg./kg. to about 125 mg./kg. per dosage, with up to six dosages, preferably three dosages, being given daily, conveniently at meal times. Thus, dosages will preferably range from 0.3 mg./kg./day to as much as 3 g./kg./day. Because of the AAL agent, such high dosages can be administered without fear of producing anal leakage effects. Dosages of less than about 0.1 mg./kg. do not materially inhibit the absorption or enhance the excretion of toxins in most patients.

The beneficial effects of the present compositions are demonstrated in the following Animal Studies.

ANIMAL STUDIES (I)

Introduction

In the following animal studies, typical polyol fatty acid polyester compositions of the type described hereinbefore were used. The studies involved feeding of a labeled model lipophilic toxin, $^{14}$C-DDT, and measurement of the amount of that pesticide absorbed, as indicated by analysis of thoracic duct lymph (48 hour collection, post meal).

Experimental Design and Methods

Six rats were provided with functioning (greater than 25 ml/24 hour) thoracic duct cannulae. Three were fed by stomach tube weighed portions of a standard emulsion diet containing as the fat component 30 ppm $^{14}$C-DDT dissolved in soybean oil (SBO). The other three rats were fed the emulsion diet with 30 ppm $^{14}$C-DDT dissolved in a 1:1 mixture of soybean oil and mixed sucrose hexa-, hepta-, and octa-esters of $C_{14}$–$C_{18}$ fatty acids as the polyol fatty acid polyester detoxifying agent. Lymph fluid was collected for 48 hours after feeding and weighed. Portions of the dietary fat/$^{14}$C-DDT solutions and aliquots of the lymph fluid were assayed for radio-activity. The results are tabulated below.

| | 48-Hr. Post-Meal Recovery of $^{14}$C-DDT in the Thoracic Duct Lymph Fluid of Rats | | | |
|---|---|---|---|---|
| Rat # | Counts Fed | Counts Recovered | Lymph Output | %$^{14}$C Recovered |
| | Diet Fat Soybean Oil | | | |
| 1 | 5,527,800 | 3,474,120 | 156.0g | 62.8 |
| 2 | 6,845,000 | 4,700,494 | 227.5g | 68.7 |
| 3 | 4,932,100 | 3,365,964 | 155.4g | 68.2 |
| | | | Avg. | 66.6 |
| | Diet Fat Soybean Oil + Polyol Fatty Acid Polyester | | | |
| 1 | 4,656,450 | 1,196,580 | 154.0g | 25.7 |
| 2 | 5,518,550 | 1,032,920 | 151.9g | 18.7 |
| 3 | 6,179,925 | 1,152,480 | 102.9g | 18.6 |
| | | | Avg. | 21.0 |

ANIMAL STUDIES (II)

Experimental Design and Methods

Three rats were gavaged with weighed portions of an emulsion diet containing the labeled model lipophilic toxin $^{14}$C-DDT, in SBO. Three other rats were similarly fed $^{14}$C-DDT in a 1:1 mixture of polyol fatty acid polyester-:SBO, using mixed sucrose hexa-, hepta-, and octaesters of $C_{14}$–$C_{18}$ fatty acids as the polyol fatty acid polyesters. Feces were collected for 72 hr. at which time the animals were sacrificed. The liver lipids, epididymal fat pads and total body fat were recovered by extraction. Aliquots of these extracts plus a sample of the $^{14}$C-DDT diet fat mixture were assayed for ratioactivity. The results are tabulated below.

| | 72 Hr. Post-Meal Distribution of $^{14}$C-DDI | | | | |
|---|---|---|---|---|---|
| Animals | Feces | Fat Pads | Liver | Carcass Fat | Total |
| | Soybean Oil as Diet Fat % Recovery | | | | |
| A-1 | 9.0 | 3.4 | 2.0 | 60.5 | 74.9 |
| A-2 | 4.5 | 5.6 | 2.4 | 59.4 | 71.8 |
| A-3 | 8.0 | 4.5 | 2.3 | 59.7 | 74.4 |
| AVERAGE | 7.2 | 4.5 | 2.3 | 59.9 | 73.7 |
| | Soybean Oil + Polyol Fatty Acid Polyester as Diet Fat | | | | |
| B-1 | 57.2 | 1.5 | 1.0 | 18.2 | 78.0 |
| B-2 | 59.1 | 1.3 | 0.8 | 19.6 | 80.8 |
| B-3 | 52.5 | 1.5 | 0.8 | 28.0 | 82.8 |
| AVERAGE | 56.3 | 1.4 | 0.9 | 21.9 | 80.5 |

INDUSTRIAL APPLICABILITY

The following, non-limiting examples further illustrate the compositions and processes of this invention. It will be appreciated that sugars and sugar alcohols, appropriately esterified, are encompassed by the term "sugar" as used herein and such materials can be interchanged in the compositions. All percentages herein are be weight, unless otherwise specified.

EXAMPLE I

Gelatin capsules for use by the patient exposed to a lipophilic organic toxin, especially DDT and Kepone, are prepared by conventional methods, as follows:

| Ingredient | Amount per Capsule |
|---|---|
| Sucrose fatty acid polyester* | 2000 mg. |
| Retinol | 0.3 RDA |
| Stearic Acid | 750 mg. |

*Liquid, mixed hexa-, hepta- and octa-sucrose esters, predominately the octa-ester, esterified with mixed soybean oil fatty acids, predominately in the $C_{16}$–$C_{18}$ chain length.

The capsules of the foregoing type are prepared by simply mixing the ingredients and filling the standard gelatin capsules. The capsules are administered orally three times daily (with each meal). This treatment regimen inhibits lipophilic toxin uptake significantly and decreases the body toxin levels of humans or lower animals exposed to lipophilic toxins. Vitamin A levels in the patients are not decreased significantly from the normal. The patients are not troubled by undesired anal leakage with this regimen.

Similar results are obtained when the sucrose polyester in the capsules of Example I is replaced with an equivalent quantity of a fatty acid polyester selected from the group consisting of glucose tetraoleate; glucose tetrastearate; mixed glucose tetraesters of soybean oil fatty acids; mixed mannose tetraesters of tallow fatty acids; mixed galactose tetraesters of olive oil fatty acids; mixed arabinose tetraesters of cottonseed oil fatty acids; xylose tetralinoleate; galactose pentastearate; sorbitol tetraoleate; sucrose tetrastearate; sucrose pentastearate; sucrose hexaoleate; sucrose heptaoleate; and sucrose octaoleate, respectively.

In the composition of Example I the retinol is replaced by an equivalent dosage level of a commercial vitamin A ester concentrate and equivalent results are secured.

In the composition of Example I, the stearic acid anti-anal leakage ingredient is replaced by an equivalent amount of methyl stearate, ethyl stearate, propyl stearate, methyl behenate, ethyl behenate, hydrogenated palm oil, hydrogenated rapeseed oil and mixed hydrogenated tallow triglycerides, respectively, and equivalent results are secured.

Preferred compositions of the type of Example I for inhibiting the absorption and enhancing the excretion of lipophilic organic toxins, especially in the human body, preferably comprise from about 0.1 gram to about 5 grams of mixed hexa-, hepta-, and octa-oleate esters of sucrose polyester, an effective amount (as disclosed hereinabove) of the AAL agent and at least about 0.1 RDA of one or more of the fat-soluble vitamins.

EXAMPLE II

Gelatin capsules comprising a unit dosage form of an AAL agent, a liquid polyester and vitamin E are prepared by conventional means, as follows:

| Ingredient | Amount per Capsule |
| --- | --- |
| Sucrose octaoleate | 3500 mg. |
| Vitamin E* | 0.2 RDA |
| Hydrogenated palm oil | 750 mg. |

*Consists of mixed alpha, beta, gamma and delta tocopherols.

The above capsules are administered orally three times daily (three per meal/70 kg. man) over a one-month period. This treatment regimen substantially inhibits lipophilic toxin uptake in the patient and enhances toxin excretion. No vitamin E deficiency in the patient is noted. No anal leakage from use of the capsules is noted.

The capsules of Example II are additionally supplemented with sufficient β-carotene to provide a 0.25 RDA of vitamin A per capsule.

The hydrogenated palm oil is replaced by an equivalent amount of tristearin and equivalent antianal leakage results are secured.

The capsules of Example II are suitable for human use and for veterinary use with horses, cattle, dogs, cats and other animals exposed to lipophilic toxins.

EXAMPLE III

Gelatin capsule comprising an AAL agent, a liquid polyester and containing a mixture of the fat-soluble vitamins are as follows:

| Ingredient | Mg. per Capsule |
| --- | --- |
| Sucrose octaoleate | 750 |
| Vitamin A | 0.1 |
| Vitamin D | 0.01 |
| Vitamin E | 0.1 |
| Vitamin K | 0.1 |
| Ethyl stearate | 750 |

The vitamin A employed in the capsules of Example III is retinol; the vitamin D is a 1:1 mixture of irradiated ergosterol and irradiated 7-dehydrocholesterol; the vitamin E comprises a commercial mixture of alpha, beta, gamma and delta tocopherols; and the vitamin K comprises the fat-soluble phylloquinone.

Three capsules of the type prepared in Example III are administered orally five times daily (three with each meal) to inhibit toxin uptake and increase toxin excretion in a 70 kg. patient exposed to lipophilic toxins such as Kepone or the PCB's. The body levels of fat-soluble vitamins A, D, E and K do not decrease below normal. No anal leakage is noted. Similar capsules in this dosage range without ethyl stearate can cause an undesired laxative effect, i.e., leakage of polyester through the anal sphincter, in some patients.

EXAMPLE IV

A highly palatable, low calorie composition suitable for use in chronic de-toxification regimens and/or as a cooking fat substitute by individuals on a prophylactic diet is as follows:

| Ingredient | % by Weight |
| --- | --- |
| Cocoa butter | 50 |
| Vitaminized liquid sucrose polyester* | 50 |

*Avg. 7.5 ester of sucrose and unsaturated, mixed soybean oil fatty acids fortified to provide 1000 I.U. of vitamin A per one ounce of composition.

The composition of the foregoing type is used in standard fashion as a cooking fat. The continued use of the composition as a replacement for regular cooking fats lowers the body's PCP (pentachlorophenol) toxin level but does not cause depletion of vitamin A in the tissues. No anal leakage of the liquid polyester is noted.

In the composition of Example IV the natural cocoa butter is replaced by an equivalent amount of the position-specific triglycerides SOO, POO, AOO, BOO, SOS, POP, AOA, BOB, OSS, PSS, ASS, and BSS, respectively, and equivalent results are secured.

The composition of Example IV is administered via nasogastric tube to a comatose patient following acute PBB toxin ingestion. Absorption of the toxin is inhibited and increased amounts of the toxin are excreted in the feces. The composition is administered to a comatose patient by gastric lavage and by enema, and equivalent results are obtained.

EXAMPLE V

A plastic shortening is prepared from the following ingredients.

| Ingredient | % by Weight |
| --- | --- |
| Cocoa butter | 40 |
| Vitaminized xylitol pentaoleate* | 50 |
| OSS | 10 |

*Vitaminized with sufficient irradiated ergosterol to provide 40.0 I.U. of vitamin D per two ounce serving.

The composition of Example V is prepared by thoroughly mixing the indicated ingredients. The composition is suitable for use in frying and other types of cooking where a plastic fat is employed. The fat composition of Example V can also be employed in the preparation of baking doughs suitable for use by the chronic detoxification patient. Continued ingestion of the plastic shortening of Example V, or foods made therefrom, reduces the body's toxin level and does not result in vitamin D deficiency. No anal leakage of the xylitol pentaoleate is noted.

The composition of Example V is added to commercial, dry animal feed compositions (15% level) to effect detoxification of sheep and cattle exposed to DDT, Kepone and the like.

EXAMPLE VI

A vitamin-fortified, non-anal leakage, low calorie, detoxification composition prepared with an edible, but non-absorbable, non-digestible, solid polyol polyester detoxifying agent is as follows:

| Ingredient | % by Weight |
|---|---|
| Vitaminized sucrose octastearate* | 100 |

*Vitamin-fortified with a commercial mixture of vitamins A, D, E and K sufficient to provide an RDA of each of these vitamins per three ounce serving.

The composition of Example VI is suitable for use as a cooling fat by the chronically contaminated patient to reduce body toxin levels while maintaining normal levels of the fat-soluble vitamins. No anal leakage is noted.

In the composition of Example VI the sucrose octastearate is replaced by an equivalent amount of sucrose heptastearate and sucrose octapalmitate, respectively, and equivalent results are secured.

The composition of Example VI is included as a fat component in animal, especially poultry, feed formulations (20% by weight of feed) and equivalent results are secured in that animals fed the modified formulations rapidly excrete ingested lipophilic toxins such as PCB, DDT, Kepone and BHC.

EXAMPLE VII

The composition of Example VI is prepared without vitamins and employed in the disclosed manner to effect detoxification in humans and lower animals.

What is claimed is:

1. A method for detoxifying humans and lower animals exposed to lipophilic toxins, comprising administering to a human or lower animal exposed to lipophilic toxins a therapeutically effective amount of a non-absorbable, non-digestible polyol fatty acid polyester having at least 4 fatty acid ester groups, wherein the polyol fatty acid polyester is selected from the group consisting of sugars and sugar alcohols containing from 4 to 8 hydroxyl groups esterified with fatty acid groups and wherein each fatty acid group has from about 8 to about 22 carbon atoms.

2. A method according to claim 1 wherein the amount administered is from about 0.3 mg. polyester per kilogram of body weight per day to about 3 gms. polyester per kilogram of body weight per day.

3. A method according to claim 2 wherein the polyol fatty acid polyester is a sucrose fatty acid polyester.

4. A method according to claim 3 wherein the sucrose fatty acid polyester is selected from the group consisting of the hexaoleate, heptaoleate, and octaoleate of sucrose, and mixtures thereof.

5. A method for detoxifying humans and lower animals exposed to lipophilic toxins with minimal anal leakage effect, comprising administering to a human or lower animal exposed to lipophilic toxins a therapeutically effective amount of a composition comprising from about 50% to about 90% by weight of a non-absorbable, non-digestible liquid polyol fatty acid polyester having at least 4 fatty acid ester groups, wherein the polyol fatty acid polyester is selected from the group consisting of sugars and sugar alcohols containing from 4 to 8 hydroxyl groups esterified with fatty acid groups and each fatty acid group has from about 8 to about 22 carbon atoms, and from about 10% to about 50% by weight of an anti-anal leakage agent selected from the group consisting of edible $C_{12}$–$C_{24}$ saturated fatty acids, and their edible salts; edible, digestible sources of $C_{12}$–$C_{24}$ saturated fatty acids; solid edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid ester group has from about 8 to about 22 carbon atoms; and edible, non-digestible esters of alpha-branched chain $C_{10}$–$C_{18}$ fatty acids.

6. A method according to claim 5 wherein the liquid polyol fatty acid polyester is a sucrose fatty acid polyester.

7. A method according to claim 6 wherein the sucrose fatty acid polyester is selected from the group consisting of the hexaoleate, heptaoleate, and octaoleate of sucrose, and mixtures thereof.

8. A method according to claim 7 wherein the anti-anal leakage agent is selected from the group consisting of: hydrogenated palm oil; natural and synthetic cocoa butter; the 1-stearoyl, 1-palmitoyl, 1-arachidoyl and 1-behenoyl 2,3-dioleins; the 2-oleoyl 1,3-distearins, 1,3-dipalmitins, 1,3-diarachidins and 1,3-dibehenins; 1-oleoyl distearin; 1-palmitoyl distearin; 1-arachidoyl distearin; and 1-behenoyl distearin; and mixtures thereof.

9. A method for detoxifying humans and lower animals exposed to lipophilic toxins without decreasing the body's stores of fat-soluble vitamins, comprising administering to a human or lower animal exposed to lipophilic toxins a therapeutically effective amount of a composition comprising a major portion of a non-absorbable, non-digestible polyol fatty acid polyester having at least 4 fatty acid ester groups, wherein the polyol fatty acid polyester is selected from the group consisting of sugars and sugar alcohols containing from 4 to 8 hydroxyl groups esterified with fatty acid groups and each fatty acid group has from about 8 to about 22 carbon atoms, and sufficient fat-soluble vitamin selected from the group consisting of vitamin A, vitamin D, vitamin E, and vitamin K, and mixtures thereof, to prevent abnormally low levels of said fat-soluble vitamins in humans or animals ingesting said composition.

10. A method according to claim 9 wherein the polyol fatty acid polyester is sucrose fatty acid polyester.

11. A method according to claim 10 wherein the sucrose fatty acid polyester is selected from the group consisting of the hexaoleate, heptaoleate, and octaoleate of sucrose, and mixtures thereof.

12. A method of detoxifying humans and lower animals exposed to lipophilic toxins without decreasing the body's stores of fat-soluble vitamins and with minimized anal leakage effect, comprising administering to a human or lower animal exposed to lipophilic toxins a therapeutically effective amount of a composition comprising:

a. a major portion of a non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid groups has from about 8 to about 22 carbon atoms;

b. a minor portion of an anti-anal leakage agent selected from the group consisting of: edible $C_{12}$–$C_{24}$ saturated fatty acids, and their edible salts; edible, digestible sources of $C_{12}$–$C_{24}$ saturated fatty acids, solid, edible, non-absorbable, non-digestible polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids; and c. sufficient fat-soluble vitamin selected from the group consisting of vitamin A, vitamin D, vitamin E and vitamin K, and mixtures thereof, to prevent abnormally low levels of said fat-soluble vitamins in animals ingesting said composition.

13. A method according to claim 12 wherein the anti-anal leakage agent is selected from the group consisting of hydrogenated palm oil; natural and synthetic cocoa butter; the 1-stearoyl, 1-palmitoyl, 1-arachidoyl and 1-behenoyl 2,3-dioleins; the 2-oleoyl 1,3-distearins, 1,3-dipalmitins, 1,3-diarachidins and 1,3-dibehenins; 1-oleoyl distearin; 1-palmitoyl distearin; 1-arachidoyl distearin; and 1-behenoyl distearin; and mixtures thereof.

14. A method according to claim 13 wherein the polyol fatty acid polyester is sucrose fatty acid polyester.

15. A method according to claim 14 wherein the sucrose fatty acid polyester is selected from the group consisting of the hexaoleate, heptaoleate, and octaoleate of sucrose, and mixtures thereof, and wherein the composition comprises at least 20% by weight of the anti-anal leakage agent.

* * * * *